(12) United States Patent
Mewshaw et al.

(10) Patent No.: US 6,541,501 B2
(45) Date of Patent: Apr. 1, 2003

(54) 2-(AMINOMETHYL)-TETRAHYDRO-9-OXA-1,3-DIAZA-CYCLOPENTA[A]-NAPHTHALENYL DERIVATIVES WITH ANTIPSYCHOTIC ACTIVITY

(75) Inventors: Richard E. Mewshaw, King of Prussia, PA (US); Rulin Zhao, Pennington, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/197,798

(22) Filed: Jul. 18, 2002

(65) Prior Publication Data

US 2003/0037701 A1 Feb. 27, 2003

Related U.S. Application Data

(60) Provisional application No. 60/306,930, filed on Jul. 20, 2001.

(51) Int. Cl.[7] ............... A61K 31/4188; C07D 235/00
(52) U.S. Cl. ............................. 514/387; 548/302.1
(58) Field of Search ............. 548/302.1; 514/387

(56) References Cited

U.S. PATENT DOCUMENTS

| | | |
|---|---|---|
| 5,318,988 A | 6/1994 | Schohe-hoop et al. |
| 5,371,094 A | 12/1994 | Heine et al. |
| 5,750,556 A | 5/1998 | Mewshaw et al. |
| 5,756,532 A | 5/1998 | Stack et al. |

FOREIGN PATENT DOCUMENTS

EP    0 771 801 A1    10/1996

OTHER PUBLICATIONS

Richard E. Mewshaw et al., Bioorg. & Med. Chem. Letters, 1999, 2593–2598, 9.
Richard E. Mewshaw et al., J. Med. Chem., 1999, 2007–2020, 42.
Richard E. Mewshaw et al., Bioorg. & Med. Chem Letters, 2002, 271–274, 12.

*Primary Examiner*—Laura L. Stockton
(74) *Attorney, Agent, or Firm*—Rebecca R. Barrett

(57) ABSTRACT

Compounds of the Formula (I):

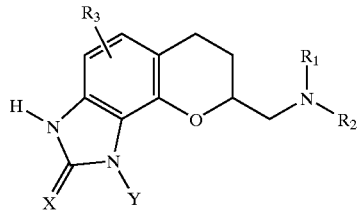

are useful in the treatment of disorders associated with brain dopamine dysregulation.

8 Claims, No Drawings

2-(AMINOMETHYL)-TETRAHYDRO-9-OXA-1,3-DIAZA-CYCLOPENTA[A]-NAPHTHALENYL DERIVATIVES WITH ANTIPSYCHOTIC ACTIVITY

This application claims priority from copending provisional application Serial No. 60/306,930, filed Jul. 20, 2001, the entire disclosure of which is hereby incorporated by reference.

BACKGROUND OF THE INVENTION

The clinical treatment of schizophrenia has long been defined by the dopamine hypothesis of schizophrenia, which holds that schizophrenia is a result of hyperactivity of dopaminergic neurotransmission, particularly in limbic brain structures such as nucleus accumbens (the mesolimbic dopamine system). Indeed, the positive symptoms of schizophrenia (hallucinations, delusions, thought disorder) are successfully treated with neuroleptics, which block dopamine receptors. However, such treatment is accompanied by the production of movement disorders or dyskinesias (extrapyramidal side effects), due to the blockade of nigrostriatal dopamine receptors. In addition, neuroleptics do not treat the negative symptoms of schizophrenia (social withdrawal, anhedonia, poverty of speech) which are related to a relative hypoactivity of neurotransmission in the mesocortical dopamine system and which respond to treatment by dopamine agonists.

Efforts to induce antipsychotic activity with dopamine autoreceptor agonists have been successful (Corsini et al., Adv. Biochem. Psychopharmacol. 16, 645–648, 1977; Tamminga et al., Psychiatry 398–402, 1986). A method for determining intrinsic activity at the dopamine D2 receptor was recently published [Lahti et al., Mol. Pharm. 42, 432–438, (1993)]. As reported, intrinsic activity is predicted using the ratio of the "low-affinity agonist" (LowAg) state of the receptor and the "high-affinity agonist" (HighAg) state of the receptor, i.e. LowAg/HighAg. These ratios correlate with agonist, partial agonist, and antagonist activities for a given compound, which activities characterize a compound's ability to elicite an antipsychotic effect.

Dopamine autoreceptor agonists produce a functional antagonism of dopaminergic neurotransmission by the reduction of neuronal firing and the inhibition of dopamine synthesis and release. Since dopamine autoreceptor agonists are partial agonists at postsynaptic dopamine receptors, they provide a residual level of stimulation sufficient to prevent the production of dyskinesias. Indeed, partial agonists are capable of functioning as either agonists or antagonists depending on the level of dopaminergic stimulation in a given tissue or brain region, and would therefore be expected to have efficacy versus both positive and negative symptoms of schizophrenia. Thus, novel dopamine partial agonists are of great interest for the treatment of schizophrenia and related disorders.

SUMMARY OF THE INVENTION

The present invention discloses compounds represented by Formula (I) which are useful antipsychotic agents:

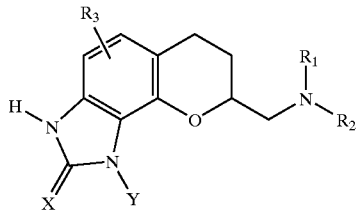

wherein:

X is O or S;

Y is H or alkyl of 1 to 10 carbon atoms;

$R_1$ is H, alkyl of 1 to 10 carbon atoms, —$CH_2$-cycloalkyl of 3 to 10 carbon atoms, —$CH_2$-bicycloalkyl of 7 to 10 carbon atoms,

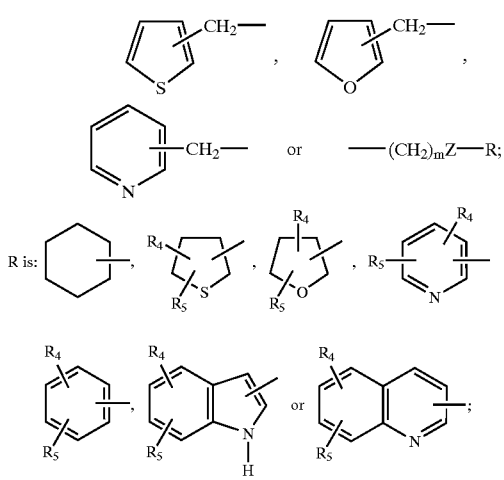

m is an integer of 0 to 4;

$R_2$ is H or alkyl of 1 to 10 carbon atoms;

$R_3$ is H, halogen, alkyl of 1 to 10 carbon atoms, —O-alkyl of 1 to 10 carbon atoms or hydroxy;

Z is O, S, or —$CH_2$—;

or $R_1$ and $R_2$ when taken together with the nitrogen atom to which they are attached form a moiety of the formula:

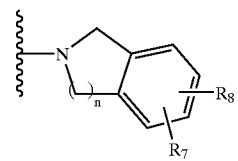

n is an integer of 1 or 2;

$R_7$ and $R_8$ are independently selected from H, halogen, alkyl of 1 to 10 carbon atoms, -0-alkyl of 1 to 10 carbon atoms or hydroxy;

$R_4$ and $R_5$ are independently hydrogen, alkyl of 1 to 10 carbon atoms, —O-alkyl of 1 to 10 carbon atoms, —S-alkyl of 1 to 10 carbon atoms, —CN, —$NO_2$, or halogen; or a pharmaceutically acceptable salt thereof.

Preferred are compounds of Formula (I) wherein $R_1$ is —$(CH2)_mZ$—R where m is 0, Z is —$CH_2$— and R is selected from the group consisting of:

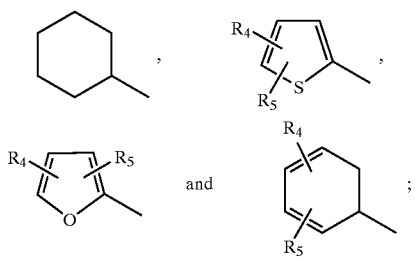

and $R_1$, $R_2$, $R_3$, $R_7$, X, Y and n are hereinbefore defined.

A particularly preferred compound of this invention according to general Formula (I) is 8-(benzylaminomethyl)-3,5,7,8-tetrahydro-9-oxa-1,3-diazacyclo-penta[a]naphthalen-2-one, and pharmaceutical salts thereof.

The present invention provides methods of treating diseases of brain dopamine dysregulation such as schizophrenia, Parkinson's disease, hyperprolactinemia, depression. Because compounds of the present invention are partial agonists at the postsynaptic dopamine $D_2$ receptor they are also useful in the treatment of alcohol and drug addiction in warm-blooded animals in need thereof. Thus, an effective amount of compound of the present invention is administered to a warm-blooded animal, preferably mammal, most preferably human.

For the compounds defined above and referred to herein, unless otherwise noted; halogen, or halo as used herein means chloro, fluoro, bromo and iodo.

Alkyl as used herein means a branched or straight chain having from 1 to 10 carbon atoms and more preferably from 1 to 6 carbon atoms. Exemplary alkyl groups include methyl, ethyl, propyl, isopropyl, butyl, isobutyl, t-butyl, pentyl and hexyl.

Cycloalkyl as used herein means a saturated ring having 3 to 10 carbon atoms and more preferably from 3 to 6 carbon atoms. Exemplary cycloalkyl rings include cyclopropyl, cyclobutyl, cyclopentyl and cyclohexyl.

The term bicycloalkyl means fused saturated bicyclic rings of 7-15 carbon atoms. Exemplary bicycloalkyl rings include bicyclo[3.3.1]nonane, bicyclo[3.3.0]octane, bicycloheptane[2.2.1], bicyclooctane[3.2.1], bicyclononane[4.3.0], and bicyclodecane[4.4.0].

Phenyl as used herein refers to a 6-membered aromatic ring.

The range of carbon atoms defines the number of carbons in the carbon backbone and does not include carbon atoms occurring in substituent groups.

It is understood by those practicing the art that the definition of compounds of Formula (I) when $R_1$, $R_2$, and $R_3$ contain asymmetric carbons, encompass all possible stereoisomers, mixtures and regioisomers thereof which possess the activity discussed below. Such regioisomers may be obtained pure by standard separation methods known to those skilled in the art. In particular, the definition encompasses any optical isomers and diastereomers as well as the racemic and resolved enantiomercially pure R and S stereoisomers as well as other mixtures of the R and S stereoisomers and pharmaceutically acceptable salts thereof, which possess the activity discussed below. Optical isomers may be obtained in pure form by standard separation techniques or enantiomer specific synthesis. It is understood that this invention encompasses all crystalline forms of compounds of Formula (I). The pharmaceutically acceptable salts of the basic compounds of this invention are those derived from such organic and inorganic acids as: lactic, citric, acetic, tartaric, fumaric, succinic, maleic, malonic, hydrochloric, hydrobromic, phosphoric, nitric, sulfuric, methanesulfonic and similarly known acceptable acids.

The present invention further provides a pharmaceutical composition which comprises a compound of Formula (I) of this invention in combination or association with a pharmaceutically acceptable carrier. In particular, the present invention provides a pharmaceutical composition which comprises an effective amount of a compound of this invention and one or more pharmaceutically acceptable carriers.

DESCRIPTION OF THE INVENTION

Compounds of Formula I are synthesized as described in Scheme I from substituted ethyl 7-hydroxy-8-nitro4-oxochromen-2-carboxylate 1 where $R_3$ is hereinbefore defined by reaction with p-toluenesulfonyl chloride to give tosylate 2. Reaction of tosylate 2 with substituted benzylamine 3 where $R_6$ is hydrogen, alkyl of 1 to 10 carbon atoms, —O-alkyl of 1 to 10 carbon atoms, halogen or —$NO_2$ at 100 to 180° C. in o-dichlorobenzene affords ethyl-7-substituted benzylamino-8-nitro-4-oxo-4H-chromene-2-carboxylate 4 where $R_3$ and $R_6$ are hereinbefore defined, followed by hydrogenation in the presence of palladium-on-carbon to give ethyl substituted-7,8-diamino-chroman-2-carboxylate 5.

The carboxylate 5 is reduced with lithium borohydride in tetrahydrofuran to give alcohol 6 where $R_3$ is hereinbefore defined. Alcohol 6 is reacted with 1,1'-carbonyidiimidazole in tetrahydrofuran to give substituted-8-hydroxymethyl-3,6,7,8-tetrahydro-1H-9-oxa-1,3-diazacyclo-penta[a]naphthalen-2-one 7 which is further reacted with p-toluenesulfonyl chloride in pyridine to give tosylate 8 where $R_3$ is hereinbefore defined. Reaction of tosylate 8 with disubstituted benzylamine 9 where $R_4$ and $R_5$ are hereinbefore defined in dimethylsulfoxide affords 8-(disubstituted aminomethyl)-3,5,7,8-tetrahydro-9-oxa-1,3-diazacyclopenta[a]-naphthalen-2-one 10.

Scheme I

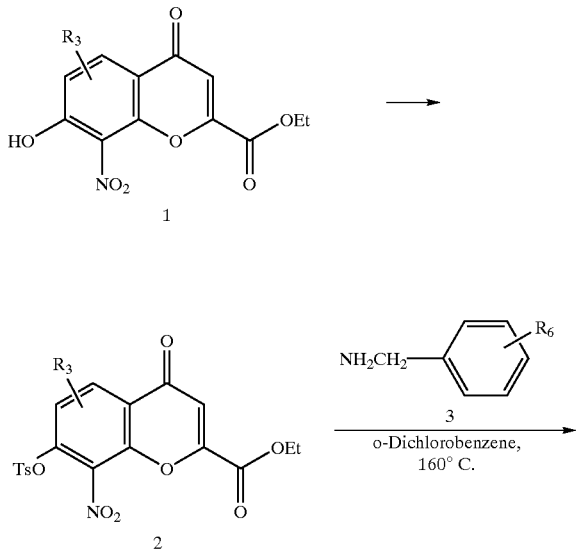

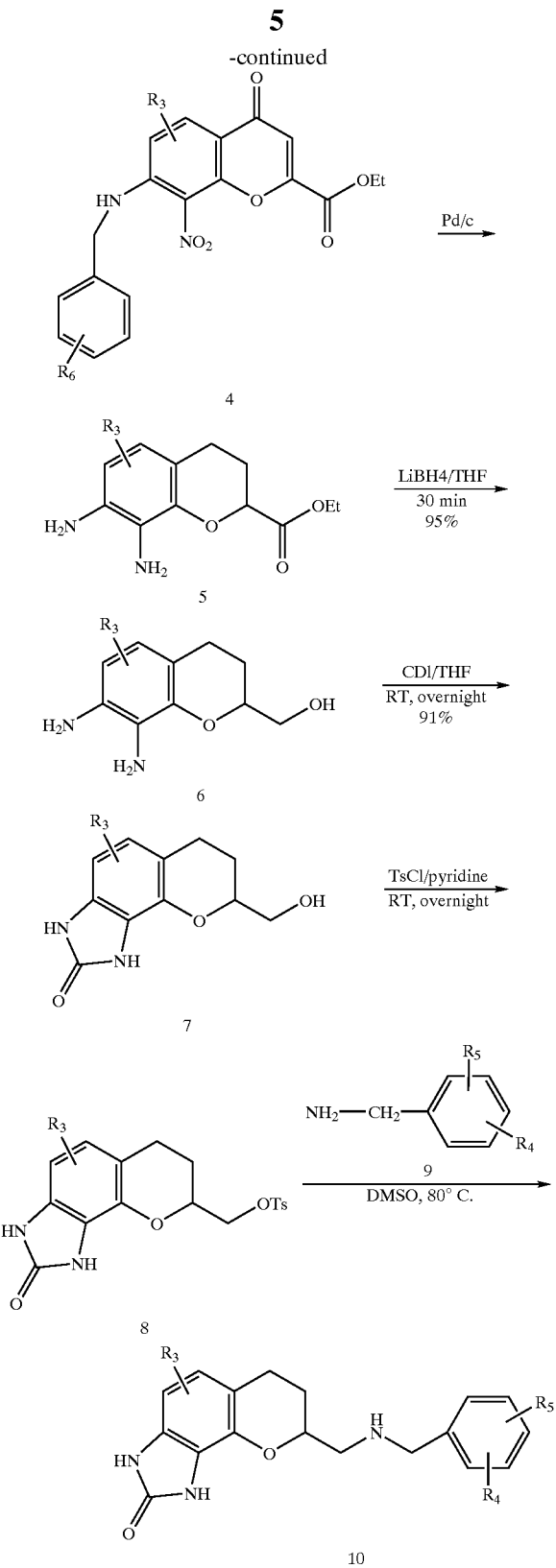

are themselves known to those of ordinary skill in this art, but are not mentioned in greater detail. Reactions are performed in a solvent appropriate to the reagents and materials employed and suitable for the transformation being effected. It is understood by those skilled in the art of organic synthesis that the various functionalities present on the molecule must be consistent with the chemical transformations proposed. This may necessitate judgement as to the order of synthetic steps, protecting groups, if required, and deprotection conditions. Substituents on the starting materials may be incompatible with some of the reaction conditions. Such restrictions to the substituents which are compatible with the reaction conditions will be apparent to one skilled in the art. Some of the compounds of the hereinbefore described schemes have centers of asymmetry. The compounds may, therefore, exist in at least two and often more stereoisomeric forms.

Affinity for the dopamine autoreceptor was established by a modification of the standard experimental test procedure of Seemen and Schaus, European Journal of Pharmacology 203: 105–109, 1991, wherein homogenized rat striatal brain tissue is incubated with [$^3$H]-quinpirole (Quin.) at various concentrations of test compound, filtered, washed and counted in a Betaplate scintillation counter.

High affinity for the dopamine $D_2$ receptor was established by the standard experimental test procedure of Fields, et al., Brain Res., 136, 5789 (1977) and Yamamura et al., ed., Neurotransmitter Receptor Binding, Chapter 9, page 171, Raven Press, N.Y. (1978) wherein homogenized limbic brain tissue is incubated with [$^3$H]-spiperidone at various concentrations of test compound, filtered washed, and shaken with Hydrofluor scintillation cocktail (National Diagnostics) and counted in a Packard 460 CD scintillation counter.

The results of the tests with compounds representative of this invention are given below.

| Example No. | $IC_{50}$ (nM) $D_2$ Quin. | $IC_{50}$ (nM) $D_2$ Spiper | Ratio |
|---|---|---|---|
| 1 | 0.29 | 89.5 | 309 |

Thus, compounds of the present invention are dopamine autoreceptor agonists which serve to modulate the synthesis and release of the neurotransmitter dopamine. The compounds are useful for the treatment of dysregulation disorders of the dopaminergic system, such as schizophrenia, schizoaffective disorders, bipolar disorders, L-DOPA induced psychoses and dyskinesias, Parkinson's disease, hyperprolactinemia, depression, and Tourette's syndrome. Compounds of the present invention are also partial agonists at the postsynaptic dopamine $D_2$ receptor and are accordingly useful in the treatment of alcohol and drug addiction, such as cocaine and analagous drugs.

The compounds of this invention may be administered orally or parenterally, neat or in combination with conventional pharmaceutical carriers. Applicable solid carriers for pharmaceutical compositions containing the compounds of this invention can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having The compounds of the present invention can be readily prepared according to hereinbefore described reaction schemes and hereinafter described examples or modifications thereof using readily available starting materials, reagents and conventional synthesis procedures. In these reactions, it is also possible to make use of variants which the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water particularly containing additives as above e.g. cellulose derivatives, preferably sodium carboxymethyl cellulose solution, alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably, the pharmaceutical composition is in unit dosage form, e.g., as tablets or capsules. In such form, the composition is sub-divided in unit dose containing appropriate quantities of the active ingredient: the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific condition must be subjectively determined by the attending physician. The variables involved include the specific psychosis and the size, age and response pattern of the patient. The treatment of substance abuse follows the same method of subjective drug administration under the guidance of the attending physician. Based upon the potency of the compounds of this invention as reported above, the human dose lies between about 5 to about 100 mg/day. As is conventional, the treatment is begun with the lower dose with gradual increase at the rate of about 5 mg/day until the desired response pattern is achieved. The optimum human dosage will lie in the range of about 15 mg/day to about 75 mg/day.

The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds.

The following examples are presented to illustrate rather than limit the methods for the production of representative compounds of the invention.

REFERENCE EXAMPLE 1

8-Nitro-4-oxo-7-(toluene-4-sulfonyloxy)-4H-chromene-2-carboxylic acid ethyl ester To a solution of ethyl 7-hydroxy-8-nitro-4-oxochromen-2-carboxylate [J.Chem. Soc. (c), 1970, 2609] ( (5.58 g, 0.02 mol) in anhydrous THF (100 mL) was added p-toluenesulfonyl chloride (7.63 g, 0.04 mol) and $K_2CO_3$ (5.52 g, 0.04 mol). The reaction mixture was allowed to stir for 12 hours at room temperature. The solution was filtered, and the filtrate was diluted with EtOAc (200 mL) and washed sequentially with saturated $NaHCO_3$ solution (30 mL) and water (2×30 mL), dried over anhydrous $Na_2SO_4$, and filtered. The solvent evaporated to give a white solid which was recrystallized from EtOAc-hexane (1:1) to give 8.15 g (94%) of the title compound: mp 125° C.; $^1$H NMR (400 MHz, $CDCl_3$): 1.39 (t, J=7Hz, 3H), 2.48, (s, 3H), 4.42 (q, J=7.0 Hz, 2H), 7.14 (s, 1H), 7.38 (d, J=9 Hz, 1H), 7.67 (d, J=9 Hz, 1H), 7.80 (d, J=9 Hz, 2H), 8.33 (d, J=9 Hz); IR: 3450, 3080, 2980, 1740, 1670, 1610, 1540, 1490, 1230 $cm^{-1}$; MS 451[$M+NH_4$].

Elemental analysis for $C_{19}H_{15}NO_9S.0.1\ CH_2Cl_2$

Calc'd: C, 51.92, H, 3.47, N 3.17

Found: C, 52.00, H, 3.48, N 3.12

REFERENCE EXAMPLE 2

Ethyl-7-benzylamino-8-nitro-4-oxo-4H-chromene-2-carboxylate

To a solution of 8-nitro-4-oxo-7-(toluene-4-sulfonyloxy)-4H-chromene-2-carboxylic acid ethyl ester (433 mg, 1 mmol) in o-dichlorobenzene was added benzylamine (214 mg, 2 mmol). The reaction mixture was heated at 170° C. for 1 hour, and the solvent was removed in vacuo to give a residue. The residue was dissolved in ethyl acetate and washed sequentially with aqueous HCl (2N 50 ml), NaOH (2N, 50 mL) and water, dried over anhydrous $Na_2SO_4$, and filtered. The solvent was evaporated in vacuo to give a solid residue. Recrystallization of the residue from ethyl acetate-hexane (2:1) provided 246 mg (67%) of the title compound: mp 168° C.; $^1$H NMR (400 MHz, $CDCl_3$): 1.43 (t, J=7 Hz, 3H), 4.45 (q, J =7.0 Hz, 2H), 4.61 (d, J=5.0 Hz, 2H), 6.90 (d, J=9.2 Hz), 7.09 (s, 1H), 7.42-7.32 (m, 5H), 8.04 (t, J=5 Hz, 1H), 8.10 (d, J=9.2 Hz, 1H); IR: 3350, 2980, 1730,1660, 1600,1420,1250 $cm^{-1}$; MS 369 [$M+H$]$^+$.

Elemental analysis for $C_{19}H_{16}N_2O_6$

Calc'd: C, 61.96, H, 4.38, N 7.61

Found: C, 61.69, H, 4.41, N 7.5

REFERENCE EXAMPLE 3

Ethyl-7,8-diamino-chroman-2-carboxylate

A mixture of ethyl-7-benzylamino-8-nitro-4-oxo-4H-chromene-2-carboxylate (1.1 g, 3 mmol), Pd/C (0.10 g, 10%), and HCl (12 N 2 mL) in ethanol (90 mL) was hydrogenated for 12 hours. The catalyst was filtered through diatomaceous earth and solvent was removed under vacuum. The residue was dissolved in EtOAc (100 mL) and then washed with saturated $NaHCO_3$ and concentrated to give 684 mg (97%) of product as a thick oil. The product was used without any further purification. $^1$H NMR (400 MHz), CDCl$_3$) δ1.26 (t, J=7.1 Hz, 3H) 2.19 (m, 2H), 2.70 (m, 1H), 3.18) bs, 4H), 4.22 (q, J=7.1 Hz, 2H), 4.66 (m, 1H), 6.30 (d, J=8 Hz, 1H), 6.40 (d, J=8 Hz,1H).

REFERENCE EXAMPLE 4

Ethyl-2-trifluoromethyl-3,6,7,8-tetrahydro-9-oxa-1,3-diaza-cyclopenta[a]-naphthalene-8-carboxylate A solution of ethyl-7,8-diamino-chroman-2-carboxylate (927 mg, 3 mmol) in trifluoroacetic acid (20 mL) was heated to reflux for 6 hours and then concentrated in vacuo to give a residue. The residue was dissolved in ethyl acetate (100 mL) and then washed with saturated NaHCO$_3$ solution (30 mL) and water (2×30 mL), dried over anhydrous Na$_2$SO$_4$. Purification by flash chromatography (30% CH$_2$Cl$_2$-hexanes) afforded 612 mg (65% yield) of the title compound as white solid: mp 134° C.; $^1$H NMR (400 MHz, CDCl$_3$) :[tautamer a]: δ:1.19 (t, J=7.1, 3H), 2.22 (m, 2H), 2.40 (m, 1H), 2.70 (m, 1H), 4.15 (q, J=7 Hz, 2H), 5.14 (m, 1H), 7.02 (d, J=8.0 Hz, 1H), 7.25 (d, J=8.0 Hz, 1H), 14.09 (bs, 1H). [tautamer b]: δ1.19 (t, J=7.1, 3H), 2.22 (m, 2H), 2.40 (m, 1H), 2.70 (m, 1H), 4.15 (q, J=7 Hz, 2H), 5.03 (m, 1H), 7.07 (s, 2H), 13.77 (bs, 1H); IR 3450, 3250, 2980, 2600, 1730, 1600, 1500, 1230 cm$^{-1}$. MS 315 [M+H]$^+$.

Elemental analysis for C$_{14}$H$_{13}$N$_2$O$_3$F$_3$. 0.1CH$_2$Cl$_2$

Calc'd: C, 52.47, H, 4.12, N 8.68

Found: C, 52.33, H, 4.11, N 8.65

REFERENCE EXAMPLE 5

(2-Trifluoromethyl-3,6,7.8-tetrahydro-9-oxa-1,3-diaza-cyclopentaralnaphthalen-8-yl)-methanol To a solution of ethyl-2-trifluoromethyl-3,6,7,8-tetrahydro-9-oxa-1,3-diaza-cyclopenta[a]naphthalene-8-carboxylate (314 mg, 1 mmol) in THF (50 mL) was added lithium borohydride (0.27 g, 3.46 mmol). The resulting solution was allowed to stir for 10 min at room temperature and then concentrated under vacuum. The residue was dissolved in ethyl acetate (100 mL) and then washed with a saturated sodium bicarbonate solution (30 mL), followed by water (2×30 mL). The solution was dried over anhydrous Na$_2$SO$_4$. and purified by flash chromatography (50% CH$_2$Cl$_2$-hexanes) to afford 171 mg (63%) of product as a white solid: mp 180° C.; $^1$H NMR (400 MHz, CDCl$_3$): 1.78 (m, 1H), 2.08 (m, 1H), 2.80 (m, 1H), 2.90 (m, 1H), 3.62 (m, 1H), 3.68 (m, 1H), 4.15 (m, 1H), 4.90 (bs, 1H, OH), 6.96 (d, J=8.4, 1H), 7.06 (d, J=8.4, 1H), 13.7 (bs, 1H); IR: 3330, 2980, 1600, 1550, 1450, 1280, 1160; MS 273 [M+H]+.

Elemental analysis for C$_{12}$H$_{11}$N$_2$O$_3$F$_3$. 0.1 CH$_2$Cl$_2$

Calc'd: C, 51.77, H, 4.02, N 9.98

Found : C, 52.07, H, 4.14, N 9.63

REFERENCE EXAMPLE 6

Toluene-4-sulfonic acid 2-trifluoromethyl-3,6,7,8-tetrahydro-9-oxa-1,3-diaza-cyclopenta[a]naphthalen-8-ylmethyl ester A solution of (2-trifluoromethyl-3,6,7,8-tetrahydro-9-oxa-1,3-diaza-cyclo-penta[a]naphthalen-8-yl)-methanol (400 mg, 1.47 mmol) and p-toluenesulfonyl chloride (344 mg, 1.76 mmol) in anhydrous pyridine (50 mL) was stirred for 12 hours and then the solvent was removed in vacuo to give a residue. The residue was dissolved in ethyl acetate (100 mL) and washed with water (3×30 mL). The organic layer was dried over anhydrous Na$_2$SO$_4$, filtered, and the solvent removed in vacuo to a residue. The residue was purified by chromatography (20% CH$_2$Cl$_2$-hexanes) to give 545 mg (87%) of the title compound as a solid: mp 160° C.; $^1$H NMR (400 MHz, CDCl$_3$): [tautamer a]:δ1.95 (m, 1H), 2.05 (m, 1H), 2.44 (s, 3H), 2.90 (m, 2H), 4.30 (m, 2H), 4.40 (m, 1H), 7.02 (d, J=8.1 Hz, 1H), 7.32 (d, J=8.1 Hz, 1H), 7.35 (d, J=8.3 Hz, 2H), 7.83 (d, J=8.3 Hz, 2H), 10.35 (bs, 1H). [tautamer b]: δ1.95 (m, 1H), 2.05 (m, 1H), 2.44 (s, 3H), 2.90 (m, 2H), 4.25 (m, 2H), 4.40 (m, 1H), 7.02 (d, J=8.1 Hz, 1H), 7.08 (d, J=8.1 Hz, 1H), 7.34 (d, J=8.3 Hz, 2H), 7.84 (d, J=8.3 Hz, 2H), 9.95 (bs, 1H); IR: 3400, 3080, 2970, 1600, 1550, 1500, 1080 cm$^{-1}$; MS 427 [M+H]$^+$.

Elemental analysis for C$_{19}$H$_{17}$N$_2$O$_4$F$_3$S.0.1 CH$_2$Cl$_2$

Calc'd: C, 52.75, H, 3.99, N 6.44

Found: C, 53.01, H, 3.96, N 6.46

REFERENCE EXAMPLE 7

(7,8-Diamino-chroman-2-yl)-methanol

To a solution of toluene-4-sulfonic acid 2-trifluoromethyl-3,6,7,8-tetrahydro-9-oxa-1,3-diazacyclopenta[a]naphthalen-8-ylmethyl ester (500 mg, 2.11 mmol) in THF (50 mL) was added lithium borohydride (2.11 mL, 2 M, 4.22 mmol). The resulting solution was stirred for 30 min at 50° C. and then evaporated in vacuo to a residue. The residue was dissolved in ethyl acetate (100 mL) and then washed with water (2×30 mL), dried over anhydrous Na$_2$SO$_4$. The solvent was removed in vacuo to afford 352 mg (86% yield) of the title compound: $^1$H NMR (400 MHz), CDCl$_3$) δ1.90 (m, 2H), 2.78 (m, 2H), 3.18 (bs, 4H), 3.78 (m, 1H, OH), 3.82 (m, 2H), 4.18 (m, 1H), 6.33 (d, J=8 Hz), 6.42 (d, J=8 Hz); MS 195 [M+H]$^+$.

REFERENCE EXAMPLE 8

8-Hydroxymethyl-3,6,7,8-tetrahydro-1H-9-oxa-1,3-diaza-cyclopenta[a]naphthalen-2-one To a solution of (7,8-diamino-chroman-2-yl)-methanol (194 mg, 1 mmol) in THF (50 mL) was added 1,1'-carbonyidiimidazole (CDI) (81 mg, 1.5 mmol). The resulting solution was stirred for 8 hours at room temperature and the solvent was evaporated in vacuo to a residue. The residue was purified by chromatography (50% CH$_2$Cl$_2$-hexanes) to give 139 mg (63% yield) of the title compound: mp 240° C.; $^1$H NMR (400 MHz, CDCl$_3$) δ1.65 (m, 1H), 2.01 (m, 1H), 2.70 (m, 2H), 3.55 (m, 1H), 3.63 (m, 1H), 4.05 (m, 1H), 4.68 (bs, 1H, OH), 6.41 (d, J=7.9, 1H), 6.60 (d, J=7.9, 1H), 10.36 (s, 1H), 10.37 (s, 1H); IR: 3250, 3080, 2980, 1700, 1500, 1210 cm$^{-1}$; MS 220 [M]$^+$.

Elemental analysis for C$_{11}$H$_{12}$N$_2$O$_3$. 0.1CH$_2$Cl$_2$

Calc'd: C, 58.29, H, 5.38, N 12.25

Found: C, 58.34, H, 5.23, N 12.16

REFERENCE EXAMPLE 9

Toluene-4-sulfonic acid-2-oxo-1,2,3,6,7,8-hexahydro-9-oxa-1,3-diaza-cyclopenta[a]naphthalen-8-ylmethyl ester A solution of 8-hydroxymethyl-3,6,7,8-tetrahydro-1H-9-oxa-1,3-diaza-cyclopenta[a]naphthalen-2-one (331 mg, 1.5 mmol) and p-toluenesulfonyl chloride (572 mg, 3 mmol) in anhydrous pyridine (50 mL) was stirred for 12 hours followed by removal of the solvent in vacuo to a residue. The residue was dissolved in ethyl acetate (100 mL) and washed with water (3×30 mL). The organic layer was dried over anhydrous Na$_2$SO$_4$ and filtered. The solvent was removed in vacuo to a residue followed by chromatography (20% CH$_2$Cl$_2$-hexanes) to afford 466 mg (83%) of the title compound as a solid: mp 205° C.; $^1$H NMR (400 MHz, CDCl$_3$): 1.87 (m, 1H), 2.02 (m, 1H), 2.48 (s, 3H), 2.81 (m, 2H), 4.22 (m, 2H), 4.31 (m, 1H), 6.56 (d, J=8.0 Hz, 1H), 6.70 (d, J=8.0 Hz, 1H), 7.38 (d, J=8.1 Hz, 2H), 7.58 (s, 1H), 7.83 (d, J=8.1 Hz, 1H), 8.18 (s, 1H); IR: 3280, 3000, 2950, 1700, 1510, 1350 cm$^{-1}$; MS 375 [M+H]$^+$.

Elemental analysis for C$_{18}$H$_{18}$N$_2$O$_5$S.0.15 CH$_2$Cl$_2$

Calc'd: C, 56.31, H, 4.76, N 7.24

Found: C, 56.31, H, 4.75, N 7.25

EXAMPLE 1

8-(Benzylamino-methyl)-3,5,7,8-tetrahydro-9-oxa-1,3-diaza-cyclopenta[a]naphthalen-2-one The title compound was prepared in same manner as Example 1 to give 101 mg (65%) product which was converted to its oxalate salt: mp 229° C. $^1$H NMR (400 MHz, DMSO-d$_6$): δ1.65 (m, 1H), 2.05 (m, 1H), 2.75 (m, 2H), 3.20 (m, 2H), 4.26 (s, 2H), 4.38 (m, 1H), 6.47 (d, J=8.1. Hz, 1H), 6.65 (d, J=8.1 Hz, 1H), 7.41 (m, 3H), 7.54 (m, 2H), 10.45 (s, 1H),.10.50 (s, 1H); IR: 3400, 3050, 2900, 1700, 1650, 1480, 1210 cm$^{-1}$; [M+H]$^+$: 310

Elemental analysis for C$_{18}$H$_{19}$N$_3$O$_2$° C.$_2$H$_4$O$_4$. 0.5H$_2$O

Calc'd: C, 58.82, H, 5.43, N 10.29

Found C, 59.10, H, 5.31, N 10.05

What is claimed is:

1. A compound of Formula I wherein:

X is O or S;

Y is H or alkyl of 1 to 10 carbon atoms;

R$_1$ is H, alkyl of 1 to 10 carbon atoms, —CH$_2$-cycloalkyl of 3 to 10 carbon atoms, —CH$_2$-bicycloalkyl of 7 to 10 carbon atoms, or —(CH$_2$)$_m$Z—R;

R is:

m is an integer of 0 to 4;

R$_2$ is H or alkyl of 1 to 10 carbon atoms;

R$_3$ is H, halogen, alkyl of 1 to 10 carbon atoms, —O-alkyl of 1 to 10 carbon atoms or hydroxy;

Z is O, S, or —CH$_2$—;

Or R$_1$ and R$_2$ when taken together with the nitrogen atom to which they are attached form a moiety of the formula:

n is an integer of 1 or 2;

R$_7$ and R$_8$ are independently selected from H, halogen, alkyl of 1 to 10 carbon atoms, -0-alkyl of 1 to 10 carbon atoms and hydroxy;

R$_4$ and R$_5$ are independently hydrogen, alkyl of 1 to 10 carbon atoms, —O-alkyl of 1 to 10 carbon atoms, —S-alkyl of 1 to 10 carbon atoms, —CN, —NO$_2$, or halogen; or a pharmaceutically acceptable salt thereof.

2. A compound of claim 1 in which R$_1$ is —(CH$_2$)$_m$Z—R; m is 0, Z is —CH$_2$— and R is selected from the group consisting of:

and or a pharmaceutically acceptable salt thereof.

3. The compound of claim 1 which is 8-(benzylamino-methyl)-3,5,7,8-tetrahydro-9-oxa-1,3-diaza-cyclopenta[a]naphthalen-2-one or a pharmaceutically acceptable salt thereof.

4. A pharmaceutical composition comprising a compound of Formula (I):

wherein:
X is O or S;
Y is H or alkyl of 1 to 10 carbon atoms;
$R_1$ is H, alkyl of 1 to 10 carbon atoms, —$CH_2$-cycloalkyl of 3 to 10 carbon atoms,
—$CH_2$-bicycloalkyl of 7 to 10 carbon atoms, R is:

m is an integer of 0 to 4;
$R_2$ is H or alkyl of 1 to 10 carbon atoms;
$R_3$ is H, halogen, alkyl of 1 to 10 carbon atoms, —O-alkyl of 1 to 10 carbon atoms or hydroxy;
Z is O, S, or —$CH_2$—;
or $R_1$ and $R_2$ when taken together with the nitrogen atom to which they are attached form a moiety of the formula:

n is an integer of 1 or 2;
$R_7$ and $R_8$ are independently selected from H, halogen, alkyl of 1 to 10 carbon atoms, -0-alkyl of 1 to 10 carbon atoms and hydroxy;
$R_4$ and $R_5$ are independently hydrogen, alkyl of 1 to 10 carbon atoms, —O-alkyl of 1 to 10 carbon atoms, —S-alkyl of 1 to 10 carbon atoms, —CN, —$NO_2$, or halogen; or a pharmaceutically acceptable salt thereof.

5. A method for treating diseases of brain dopamine dysregulation, which comprises administering to a subject in need thereof an effective amount of a compound of Formula I wherein:
X is O or S;
Y is H or alkyl of 1 to 10 carbon atoms;
$R_1$ is H, alkyl of 1 to 10 carbon atoms, —$CH_2$-cycloalkyl of 3 to 10 carbon atoms,
—$CH_2$-bicycloalkyl of 7 to 10 carbon atoms, R is:

m is an integer of 0 to 4;
$R_2$ is H or alkyl of 1 to 10 carbon atoms;
$R_3$ is H, halogen, alkyl of 1 to 10 carbon atoms, -0-alkyl of 1 to 10 carbon atoms or hydroxy;
Z is O, S, or —$CH_2$—;
or $R_1$ and $R_2$ when taken together with the nitrogen atom to which they are attached form a moiety of the formula:

n is an integer of 1 or 2;
$R_7$ and $R_8$ are independently selected from H, halogen, alkyl of 1 to 10 carbon atoms, -0-alkyl of 1 to 10 carbon atoms and hydroxy;
$R_4$ and $R_5$ are independently hydrogen, alkyl of 1 to 10 carbon atoms, —O-alkyl of 1 to 10 carbon atoms, —S-alkyl of 1 to 10 carbon atoms, —CN, —$NO_2$, or halogen; or a pharmaceutically acceptable salt thereof.

6. The method of claim 5 wherein the disease of brain dopamine dysregulation is schizophrenia, Parkinson's disease, hyperprolactinemia, depression or Tourette's syndrome.

7. The method of claim 6 wherein the disease of brain dopamine dysregulation is schizophrenia.

8. The method of claim 5 wherein the disease of brain dopamine dysregulation is alcohol or drug addiction.

* * * * *